United States Patent [19]

Kubota et al.

[11] Patent Number: 5,326,895
[45] Date of Patent: Jul. 5, 1994

[54] 3-(VINYLBENZYLOXY)PROPYLSILANE COMPOUNDS

[75] Inventors: Tohru Kubota; Toshinobu Ishihara; Mikio Endo; Katsuhiro Uehara, all of Jouetsu, Japan

[73] Assignee: Shin-Etsu Chemical Co., Ltd., Tokyo, Japan

[21] Appl. No.: 976,845

[22] Filed: Nov. 16, 1992

Related U.S. Application Data

[62] Division of Ser. No. 813,612, Dec. 26, 1991, abandoned.

[30] Foreign Application Priority Data

Dec. 26, 1990 [JP] Japan ................ 2-413948
Dec. 9, 1991 [JP] Japan ................ 3-350090

[51] Int. Cl.$^5$ .................. C07F 7/08; C07F 7/18
[52] U.S. Cl. .................. 556/445; 556/471; 556/479
[58] Field of Search .......... 556/445, 479, 471

[56] References Cited

U.S. PATENT DOCUMENTS

| 4,985,577 | 1/1991 | Shinohara et al. | 556/445 |
| 5,068,382 | 11/1991 | Rauleder et al. | 556/445 |
| 5,117,028 | 5/1992 | Knorr | 556/445 |
| 5,153,292 | 10/1992 | Liu | 556/445 X |

OTHER PUBLICATIONS

Noll, Chemistry and Technology of Silicones, Academic Press, New York(1968), p. 81.

Primary Examiner—Paul F. Shaver
Attorney, Agent, or Firm—Millen, White, Zelano & Branigan

[57] ABSTRACT 3-(Vinylbenzyloxy)propylsilane compounds represented by the general formula, $CH_2 CH\Phi CH_2 OCHCH_2 CH_2 SiR^1{}_n(OR^2)_{3-n}$ (wherein $R^1$ and $R^2$ each represent a hydrocarbon residue containing 1 to 4 carbon atoms, and n represents an integer from 0 to 2) are provided as novel styrene skeleton-containing alkoxysilane compounds which are highly useful as silane coupling agent or polymerizing monomer.

17 Claims, No Drawings

3-(VINYLBENZYLOXY)PROPYLSILANE COMPOUNDS

This is a division of application Ser. No. 07/813,612 filed Dec. 26, 1991, now abandoned.

FIELD OF THE INVENTION

The present invention relates to novel silane compounds and, more particularly, to compounds having a styrene skeleton which are highly homo- and copolymerizable, so that they are useful as a silane coupling agent, polymerizing monomers or the like.

BACKGROUND OF THE INVENTION

Hitherto known alkoxysilane compounds of the type which contain a styrene skeleton are vinylbenzyltrimethoxysilane (Masanori Kokubo et al., *Kohbunshi Ronbunshu*, volume 36, page 201 (1981)), vinyl phenyltrimethoxysilane (Y. Kawakami et al., *Polymer Journal*, volume 17, page 1159 (1985)) and so on. In the syntheses thereof, however, it is necessary to use styrene type Grignard reagents which are quite unstable and liable to polymerize (namely, vinylbenzylmagnesium halide in the former compound, and vinylphenylmagnesium halide in the latter compound). Therefore, the syntheses of such compounds on an industrial scale are very difficult. In addition, since the syntheses of the foregoing compounds require a large quantity of solvent and a process of removing salts through filtration, they are at a disadvantage in entailing high cost of manufacturing.

As for another styrene skeleton-containing alkoxysilane, vinylphenetyltrimethoxysilane is known to be obtained by hydrosilylation of divinylbenzene with a hydrogensilane (G. Greber, *Makromol. Chem.*, volume 53, page 19 (1962)). In general, the hydrosilylation method is said to be suitable for syntheses of functional group-containing alkoxysilanes in respects of low cost and good working efficiency, because it does not use any solvent and does not require any filtration process. In case of the above-cited compound, however, divinylbenzene used as a starting material is extremely unstable and apt to polymerize and, what is worse, it has a disadvantage in that there is a tendency for addition of two silane molecules upon hydrosilylation because of the presence of two vinyl groups almost equivalent in reactivity in the substrate, whereby a yield of the intended compound is lowered.

As a result of our intensive study with the intention of obviating the above-described defects, it has been found that the hydrosilylation can be effected with ease by the use of 3-(vinylbenzyloxy)-1-propenes as a starting material and can provide styrene skeleton-containing alkoxysilane compounds at a low price, and the compounds obtained herein are novel compounds, thus achieving the present invention.

SUMMARY OF THE INVENTION

Therefore, an object of the present invention is to provide novel styrene skeleton-containing alkoxysilane compounds which are useful for a silane coupling agent or as polymerizing monomers.

The above-described object is attained with 3-(vinylbenzyloxy) propylsilane compounds represented by the following general formula (1), and with methods adopted in manufacturing them;

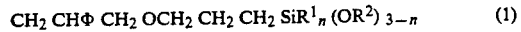

(wherein Φ represents a benzene ring; $R^1$ and $R^2$ are each a hydrocarbon residue containing 1 to 4 carbon atoms, with specific examples including methyl group, ethyl group, propyl group, isopropyl group and butyl group; n is 0, 1 or 2).

The 3-(vinylbenzyloxy)propylsilane compounds of the present invention are styrene skeleton-containing alkoxysilane compounds which can be easily synthesized by hydrosilylation reaction of 3-(vinylbenzyloxy)-1-propenes, which are ease in preparation and stable, with hydrogensilanes in the absence of a solvent without producing by-products including a salt.

DETAILED DESCRIPTION OF THE INVENTION

The compounds of the present invention can be easily manufactured using as a starting compound 3-(vinylbenzyloxy)-1-propenes represented by the following formula (2):

$$CH_2 CH\Phi CH_2 OCH_2 CH=CH_2 \qquad (2)$$

The 3-(vinylbenzyloxy)-1-propenes represented by the above formula (2) can be synthesized with ease using a known method (G. F. Dalelio et al., *Journal of Polymer Science*, volume 5, page 1245 (1867). In these compounds, it is feasible to selectively hydrosilylate only the intended double bond in the allyloxy group since the double bond in the allyloxy group is more susceptible to hydrosilylation than the vinyl group in the styrene skeleton. More specifically, the compounds represented by the general formula (2) include 3-(2-vinylbenzyloxy)-1-propene, 3-(3-vinylbenzyloxy)-1-propene and 3-(4-vinylbenzyloxy)-1-propene.

The 3-(vinylbenzyloxy)propylsilane compounds of the present invention can be synthesized using two methods described below. Additionally, $R^1$, $R^2$ and n used in the following formulae have the same meanings as those described in the foregoing general formula (1), respectively.

In a first synthesis method, the 3-(vinylbenzyloxy)propylsilane compounds of the present invention are obtained by allowing the 3-(vinylbenzyloxy)-1-propene compounds represented by the formula (2) to undergo a hydrosilylation reaction with hydrogensilanes represented by the general formula (3) in the presence of a platinum catalyst:

Examples of a compound represented by the foregoing general formula (3) include alkoxysilane compounds such as trimethoxysilane, methyldiethoxysilane, ethyldiethoxysilane and dimethylbutoxysilane.

In a second synthesis method, 3-(vinylbenzyloxy)propylhalogenosilane compounds represented by the general formula, $CH_2CH\Phi\ CH_2\ OCH_2\ CH_2\ CH_2\ SiR^1_nX_{3-n}$, are firstly prepared by allowing the 3-(vinylbenzyloxy)-1-propene compounds to undergo a hydrosilylation reaction with hydrogensilanes represented by the general formula (4) in the presence of a platinum catalyst:

wherein X represents a halogen atom.

As for the compounds represented by the foregoing formula (4), chlorosilane compounds such as trichlorosilane, methyldichlorosilane, ethyldichlorosilane and dimethylchlorosilane can be given as examples.

Then, the compounds obtained are made to react with alcohols represented by the general formula (5) to yield the 3-(vinylbenzyloxy) propylsilane compounds of the present invention:

$$R^2 OH \tag{5}$$

As for the alcohols represented by the foregoing general formula (5), methanol, ethanol, propanol, isopropanol, butanol and so on can be given as examples.

Specifically, the 3-(vinylbenzyloxy)propylsilane compounds of the present invention include 3-(4-vinylbenzyloxy)propyltrimethoxysilane, 3-(4-vinylbenzyloxy)propylmethyldimethoxysilane, 3-(4-vinylbenzyloxy)-propylmethyldiethoxysilane, 3-(3-vinylbenzyloxy)-propylethyldimethoxysilane, and 3-(2-vinylbenzyloxy)-propyldimethylbutoxysilane.

In both first and second synthesis methods, it is desirable that a reactor equipped with a stirrer, a thermometer, a reflux condenser and a dropping funnel should be used.

An amount of the platinum catalyst used is 5 to 500 ppm to the 3-(vinylbenzyloxy)-1-propene compound used, and the hydrogensilanes represented by the general formulae (3) and (4) are each dropped in an amount of 1–1.5 equivalents to the 3-(vinylbenzyloxy)-1-propene compound used. It is to be desired that these reactions should be carried out at 50°–150° C.

It deserves special emphasis that the reaction of a 3-(vinylbenzyloxy)propylhalogenosilane compound with an alcohol, which comprises the second synthesis method, can be effected without using any solvent, provided that 1.1–2 equivalents of an alcohol is used together with 1–1.5 equivalents (to the halogen atom) of urea. Additionally, the urea hydrochloride-alcohol phase can be removed using a liquid separation procedure.

The 3-(vinylbenzyloxy)propylsilane compounds of the present invention are of industrially great usefulness as a silane coupling agent for bringing about an improvement in characteristics of composite materials, or as polymerizing monomers.

When the compounds of the present invention are used as silane coupling agent, they can properly perform a function as treatment agent or additive for inorganic materials such as glass fiber, clay, silica, quartz powder, mica, alumina, etc. and for organic materials such as polyethylene, polypropylene, polystyrene, unsaturated polyester, natural rubber, synthetic rubber, etc. Therein, they can widely exert their effect upon improvements in characteristics of composite materials, including enhancement of mechanical strength and adhesiveness, stabilization of electric characteristics, reforming of their resinous component and surface modification, or fully achieve their effect as a primer for heightening adhesion power of sealing agents.

On the other hand, when the compounds of the present invention are used as polymerizing monomer, it can undergo radical copolymerization with various kinds of radical polymerizing monomers, e.g., styrenes, acrylates, methacrylates, vinyl esters, ethylene, propylene, vinyl chloride, butadiene, isoprene, chloroprene, α-olefins and so on, in the presence of a polymerization initiator such as an organic peroxide, an azo compound or so on to produce polymers containing hydrolizable alkoxysilyl groups in the side chains. These polymers have not only the property of being cross-linked efficiently with water under a mild condition, but also great adhesiveness to various kinds of substrates because they contain alkoxy groups excellent in affinity for inorganic and metallic materials. In addition, their physical properties, including heat resistance, weather resistance, gas perviousness, shock resistance and so on, are highly satisfactory. Therefore, they can also be applied to high functional plastic materials and functional film materials.

EXAMPLES

The present invention is illustrated in greater detail by reference to the following examples. However, the invention should not be construed as being limited to these examples.

EXAMPLE 1

After 691.0 g (5.0 mole) of a 50% 2-propenyl alcohol solution of sodium 2-propenoxide, 16.0 g of tetrabutylammonium bromide and 1.0 g of BHT were placed and mixed in a 3-liter glass flask equipped with a stirrer, a reflux condenser, a thermometer and a dropping funnel, 763.0 g (5.0 mole) of 4-vinylbenzyl chloride was added dropwise to the mixture from the dropping funnel as the temperature was kept at 35°–40° C. to make them undergo the reaction. At the conclusion of the reaction, water was added to dissolve the produced salt. The resulting organic phase was separated, and then distilled to collect a 83°–84° C./2 mmHg fraction. Thus, 795.4 g of 3-(4-vinylbenzyloxy)-1-propene was obtained in a 91.3% yield.

Subsequently, a 174.2 g (1.0 mole) portion of the thus obtained 3-(4-vinylbenzyloxy)-1-propene, 0.2 g of a 4% isopropyl alcohol solution of H$_2$PtCl$_6$ and 0.5 g of BHT were placed in a 500-ml glass flask equipped with a stirrer, a reflux condenser, a thermometer and a dropping funnel. Thereto, 122.2 g (1.0 mole) of trimethoxysilane was added dropwise from the dropping funnel over a 2-hour period as the reaction mixture was kept at 70°–80° C. Then, the resulting solution was ripened for 30 minutes at 80° C. The thus obtained solution was distilled to yield 265.8 g of the intended compound having a boiling point of 143°–147° C./2 mmHg. The yield thereof was 88.0%.

The results of mass spectrum (MS), nuclear magnetic resonance spectrum (NMR) and infrared absorption spectrum measurements of this compound are shown below.

Nuclear Magnetic Resonance Spectrum (NMR):

a: 3.43 ppm (S), b: 0.45–0.73 ppm (M), c: 1.30–1.88 ppm (M), d: 3.31 ppm (T), e: 4.34 ppm (S), f: 7.05–7.35 ppm (M), g: 6.56 ppm (M), h: 5.09 ppm (M), i: 5.55 ppm (M).

Herein, S and M in parentheses symbolize Singlet and Multplet, respectively.

This result is in good accordance with the theoretical spectrum of the compound having the following structural formula;

```
         (g)   (f)
  (h) H   H
      \   |    H   H
       C=C
      /   |                       CH₂OCH₂CH₂CH₂Si(OCH₃)₃
  (i) H                           (e) (d) (c) (b)   (a)

H   H
           (f)
```

Mass Spectrum (MS): m/z (relative intensity of spectral line, assignment):
296 (8, M⁻), 264 (52, M-CH₃ OH), 147 (15), 121 (100, Si(OCH₃)₃), 117 (71), 91 (49).

This result is in good accordance with the theoretical spectrum of the above-illustragted compound.

Infrared Absorption Spectrum (IR): (cm⁻¹):
2949, 2830, 1630, 1515, 1460, 1410, 1360, 1200, 1090, 990, 910.

This result is also in good accordance with the predictable spectrum of the foregoing compound.

Thus, the obtained substance is confirmed to be the compound represented by the following formula:

CH₂=CH—⌬—CH₂OCH₂CH₂CH₂Si(OCH₃)₃

EXAMPLE 2

In the same manner as in Example 1, except that 134.3 g (1.0 mole) of methyldiethoxysilane was used in the place of 122.2 g (1.0 mole) of trimethoxysilane, 256.4 g of a compound having a boiling point of 148°–151° C./2 mmHg was obtained in a 83.1% yield.

The results of mass spectrum (MS), nuclear magnetic resonance spectrum (NMR) and infrared absorption spectrum measurements of this compound are shown below.

Nuclear Magnetic Resonance Spectrum (NMR):
a: 1.09 ppm (T), b: 3.59 ppm (Q), c: −0.03 ppm (S), d: 0.38–0.63 ppm (M), e: 1.30–1.78 ppm (M), f: 3.25 ppm (T), g: 4.29 ppm (S), h: 6.97–7.25 ppm (M), i: 6.52 ppm (M), j: 5.02 ppm (M), k: 5.50 ppm (M).

Herein, S, M, T and Q in parentheses symbolize Singlet, Multiplet, Triplet; and Quartet, respectively.

This result is in good accordance with the theoretical spectrum of the compound having the following structural formula;

```
          (i)  (h)
  (j) H    H
      \    |    H   H
       C=C                                    (c)
      /    |                                  CH₃
  (k) H                                       |
                 —⌬—CH₂OCH₂CH₂CH₂Si(OCH₂CH₃)₂
                       (g)  (f) (e) (d)    (b)  (a)

H   H
           (h)
```

Mass Spectrum (MS): m/z (relative intensity of spectral line, assignment):

308 (1, M⁻), 262 (79, M-CH₃ CH₂ OH), 145 (10), 133 (63, SiMe(OCH₂CH₃)₂), 117 (100), 105 (15), 89 (14).

This result is in good accordance with the theoretical spectrum of the above-illustrated compound.

Infrared Absorption Spectrum (IR): (cm⁻¹):
2970, 2940, 2870, 1630, 1520, 1450, 1400, 1360, 1260, 1170, 1110, 1080, 995, 950.

This result is also in good accordance with the predictable spectrum of the foregoing compound.

Thus, the obtained substance is confirmed to be the compound represented by the following formula:

CH₂CH—⌬—CH₂OCH₂CH₂CH₂SiCH₃(OCH₂CH₃)₂

EXAMPLE 3

87.1 g (0.5 mole) of 3-(4-vinylbenzyloxy)-1-propene, 0.1 g of a 4% isopropyl alcohol solution of H₂ PtCl₆ and 0.5 g of BHT were placed in a 500-ml glass flask equipped with a stirrer, a reflux condenser, a thermometer and a dropping funnel. Thereto, 57.5 g (0.5 mole) of methyldichlorosilane was added dropwise from the dropping funnel over a 2-hour period as the reaction mixture was kept at 70°–80° C. Then, the resulting solution was ripened for 30 minutes at 80° C. To the resulting solution, 66.1 g (1.1 moles) of urea was added, and 48.1 g (1.5 moles) of methanol was further added dropwise under room temperature. Thereupon, the urea hydrochloride-methanol phase was separated to form the lower layer. The lower layer was removed, while the upper layer was distilled to give 121.0 g of a compound having a boiling point of 147°–151° C./2 mmHg. This compound was identified as the compound prepared in Example 2 by the measurements of mass spectrum (MS), nuclear magnetic resonance spectrum (NMR) and infrared absorption spectrum thereof. The yield in this preparation process was 78.4%.

What is claimed is:

1. A method of manufacturing 3-(vinylbenzyloxy)-propylsilane compounds, comprising:
   subjecting at least one 3-(vinylbenzyloxy)-1-propene compound represented by the formula, CH₂CHΦCH₂OCH₂CHCH₂, wherein Φ is a benzene ring, and at least one hydrogensilane represented by the formula HSiR$_n^1$ (OR²)$_{3-n}$, wherein R¹ and R² are each a hydrocarbon residue containing 1 to 4 carbon atoms, and n is 0, 1 or 2, to a hydrosilylation reaction in the presence of a platinum catalyst.

2. A method according to claim 1, wherein said at least one 3-(vinylbenzyloxy)-1-propene compound is 3-(2-vinylbenzyloxy)-1-propene, 3-(3-vinylbenzyloxy)-1-propene or 3-(4-vinylbenzyloxy)-1-propene.

3. A method according to claim 1, wherein said at least one hydrogensilane is an alkoxysilane.

4. A method according to claim 3, wherein said alkoxysilane is trimethoxyhydrogensilane, methyldiethoxyhydrogensilane, ethyldiethoxyhydrogensilane or dimethylbutoxyhydrogensilane.

5. A method according to claim 1, wherein the amount of hydrogensilane used is 1–1.5 equivalents relative to the amount of 3-(vinylbenzyloxy)-1-propene compound.

6. A method according to claim 1, wherein the amount of said platinum catalyst used is 5-500 ppm relative to the amount of 3-(vinylbenzyloxy)-1-propene compound.

7. A method of manufacturing 3-(vinylbenzyloxy)propylsilane compounds, comprising:
preparing at least one 3-(vinylbenzyloxy)propylhalogenosilane compound represented by the formula, $CH_2CH\Phi CH_2OCH_2CH_2CH_2SiR_n^1X_{3-n}$, wherein $\Phi$ is a benzene ring, $R^1$ is a hydrocarbon radical containing 1 to 4 carbon atoms, X is a halogen atom, and n is 0, 1 or 2, by subjecting at least one 3-(vinylbenzyloxy)-1-propene compound to a hydrosilylation reaction with at least one hydrogensilane represented by formula, $HSiR_n^1X_{3-n}$ wherein $R^1$, X and n have the same meaning as described above, in the presence of a platinum catalyst; and
reacting said at least one 3-(vinylbenzyloxy)propylhalogenosilane with at least one alcohol represented by the formula $R^2OH$, wherein $R^2$ is a hydrocarbon residue containing 1 to 4 carbon atoms.

8. A method according to claim 7, wherein said at least one 3-(vinylbenzyloxy)-1-propene compound is 3-(2-vinylbenzyloxy)-1-propene, 3-(3-vinylbenzyloxy)-1-propene or 3-(4-vinylbenzyloxy)-1-propene.

9. A method according to claim 7, wherein X is a chlorine atom.

10. A method according to claim 7, wherein said at least one hydrogensilane is trichlorosilane, methyldichlorosilane, ethyldichlorosilane or dimethylchlorosilane.

11. A method according to claim 7, wherein the amount of said hydrogensilane used is 1-1.5 equivalents relative to the amount of 3-(vinylbenzyloxy)-1-propene compound.

12. A method according to claim 7, wherein the amount of said platinum catalyst used is 5-500 ppm relative to the amount of 3-(vinylbenzyloxy)-1-propene compound.

13. A method according to claim 7, wherein said reaction of 3-(vinylbenzyloxy)propylhalogenosilane with alcohol is carried out using 1-1.5 equivalents, relative to the halogen atom, of urea together with the alcohol and controlling the amount of the alcohol to 1.1-2 equivalents, relative to the halogen atom, to effect the reaction without using any other solvent.

14. A method according to claim 1, wherein said 3-(vinylbenzyloxy)propylsilane is 3-(4-vinylbenzyloxy)propyltrimethoxysilane, 3-(4-vinylbenzyloxy)propylmethyldimethoxysilane, 3-(4-vinylbenzyloxy)propylmethyldiethoxysilane, 3-(3-vinylbenzyloxy)propylethyldimethoxysilane or 3-(2-vinylbenzyloxy)propyldimethylbutoxysilane.

15. A method according to claim 1, wherein said hydrosilylation reaction is conducted at 50°-150° C.

16. A method according to claim 7, wherein said 3-(vinylbenzyloxy)propylsilane is 3-(4-vinylbenzyloxy)propyltrimethoxysilane, 3-(4-vinylbenzyloxy)propylmethyldimethoxysilane, 3-(4-vinylbenzyloxy)propylmethyldiethoxysilane, 3-(3-vinylbenzyloxy)propylethyldimethoxysilane or 3-(2-vinylbenzyloxy)propyldimethylbutoxysilane.

17. A method according to claim 1, wherein said hydrosilylation reaction is conducted at 50°-150° C.

* * * * *